(12) United States Patent
Sasing et al.

(10) Patent No.: US 8,273,092 B2
(45) Date of Patent: Sep. 25, 2012

(54) INTRAMEDULLARY NAIL DISTAL TARGETING DEVICE

(75) Inventors: Jude L. Sasing, Quezon (PH); Aristedes C. Dayanghirang, Manitoba (CA); Dennis Alphonse Yap, Antipolo (PH); Ramon B. Gustilo, Eden Prairie, MN (US); Francis O. Chan, Cagayan (PH); Roberto R. Fresnido, Jr., Rizal (PH)

(73) Assignee: Orthopaedic International, Inc., Cabuyao (PH)

( * ) Notice: Subject to any disclaimer, the term of this patent is extended or adjusted under 35 U.S.C. 154(b) by 1297 days.

(21) Appl. No.: 11/887,689

(22) PCT Filed: Nov. 21, 2005

(86) PCT No.: PCT/PH2005/000023
§ 371 (c)(1),
(2), (4) Date: Oct. 2, 2007

(87) PCT Pub. No.: WO2006/107222
PCT Pub. Date: Oct. 12, 2006

(65) Prior Publication Data
US 2009/0069816 A1 Mar. 12, 2009

(30) Foreign Application Priority Data
Apr. 5, 2005 (PH) ............................ 1-2005-000176

(51) Int. Cl.
*A61B 17/58* (2006.01)
*A61B 17/60* (2006.01)
*A61F 2/00* (2006.01)
(52) U.S. Cl. .......................................... 606/98; 606/96
(58) Field of Classification Search .................... 606/62, 606/64, 96, 98
See application file for complete search history.

(56) References Cited

U.S. PATENT DOCUMENTS

| | | | |
|---|---|---|---|
| 3,814,089 A | 6/1974 | Deyerle | |
| 4,621,628 A | 11/1986 | Brudermann | |
| 4,667,664 A | 5/1987 | Taylor et al. | |
| 4,881,535 A | 11/1989 | Sohngen | |
| 4,911,153 A * | 3/1990 | Border ............................ | 606/98 |
| 4,913,137 A | 4/1990 | Azer et al. | |
| 5,127,913 A | 7/1992 | Thomas, Jr. | |
| 5,268,000 A | 12/1993 | Ottieri et al. | |
| 5,281,224 A | 1/1994 | Faccioli et al. | |
| 5,352,228 A | 10/1994 | Kummer et al. | |
| 5,374,271 A | 12/1994 | Hwang | |

(Continued)

*Primary Examiner* — Thomas Barrett
*Assistant Examiner* — Christine Nelson
(74) *Attorney, Agent, or Firm* — Kagan Binder, PLLC

(57) ABSTRACT

The present invention relates to an intramedullary nail distal targeting device (20) adapted to be installed to an external jig system (A) having a proximal attachment (B) to support an intramedullary nail (C) thereon and an extension arm (D) secured to the proximal attachment (B), the nail distal targeting device including a drill guide (21) being defined by an abbreviated cylindrical body (23) having at least a pair of guide slots (24, 24') each of the guide slots (24, 24') having a scalloped inner surface (25), an attaching mechanism (22) being provided at the upper portion of the drill guide (21), the attaching mechanism (22) secured in a rotating and sliding manner to a distal end of the extension arm (D) and at least a pair of guide sleeves (10, 10') being telescopically fitted correspondingly into the slots (24, 24') of the drill guide (21), each of the guide sleeves (10, 10') having a scalloped outer surface to correspondingly fit into the guide slots (24, 24'), each of the guide sleeves (10, 10') being provided with aligned and spaced apart drill-guiding holes (13, 14, 15) extended between the opposed end portions thereof.

5 Claims, 10 Drawing Sheets

U.S. PATENT DOCUMENTS

| | | |
|---|---|---|
| 5,766,179 A | 6/1998 | Faccioli et al. |
| 6,027,506 A | 2/2000 | Faccioli et al. |
| 6,093,192 A * | 7/2000 | Abel .............................. 606/98 |
| 6,106,528 A | 8/2000 | Durham et al. |
| 6,746,453 B2 * | 6/2004 | Deloge et al. .................. 606/98 |
| 2004/0082955 A1 * | 4/2004 | Zirkle, Jr. ....................... 606/62 |

\* cited by examiner

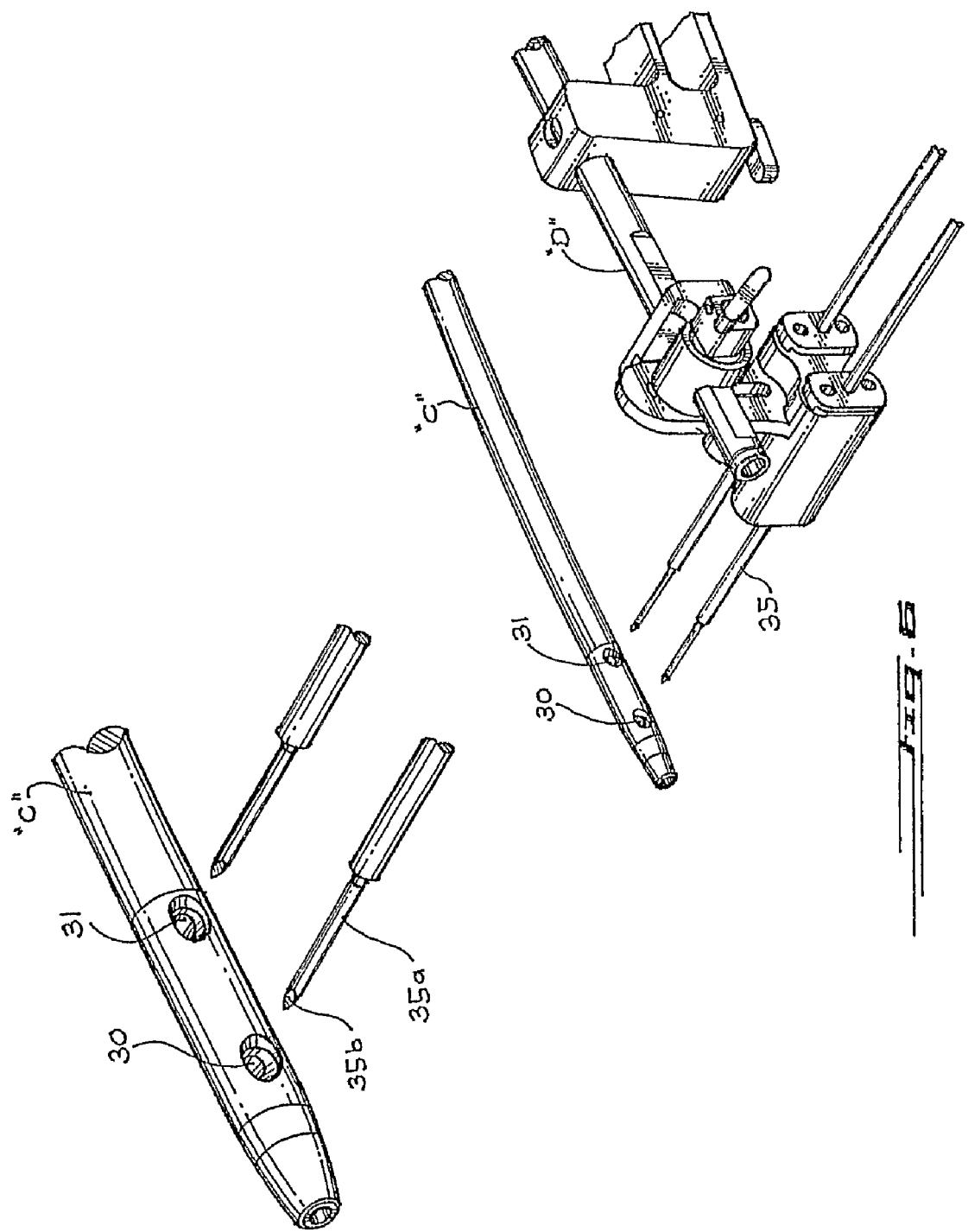

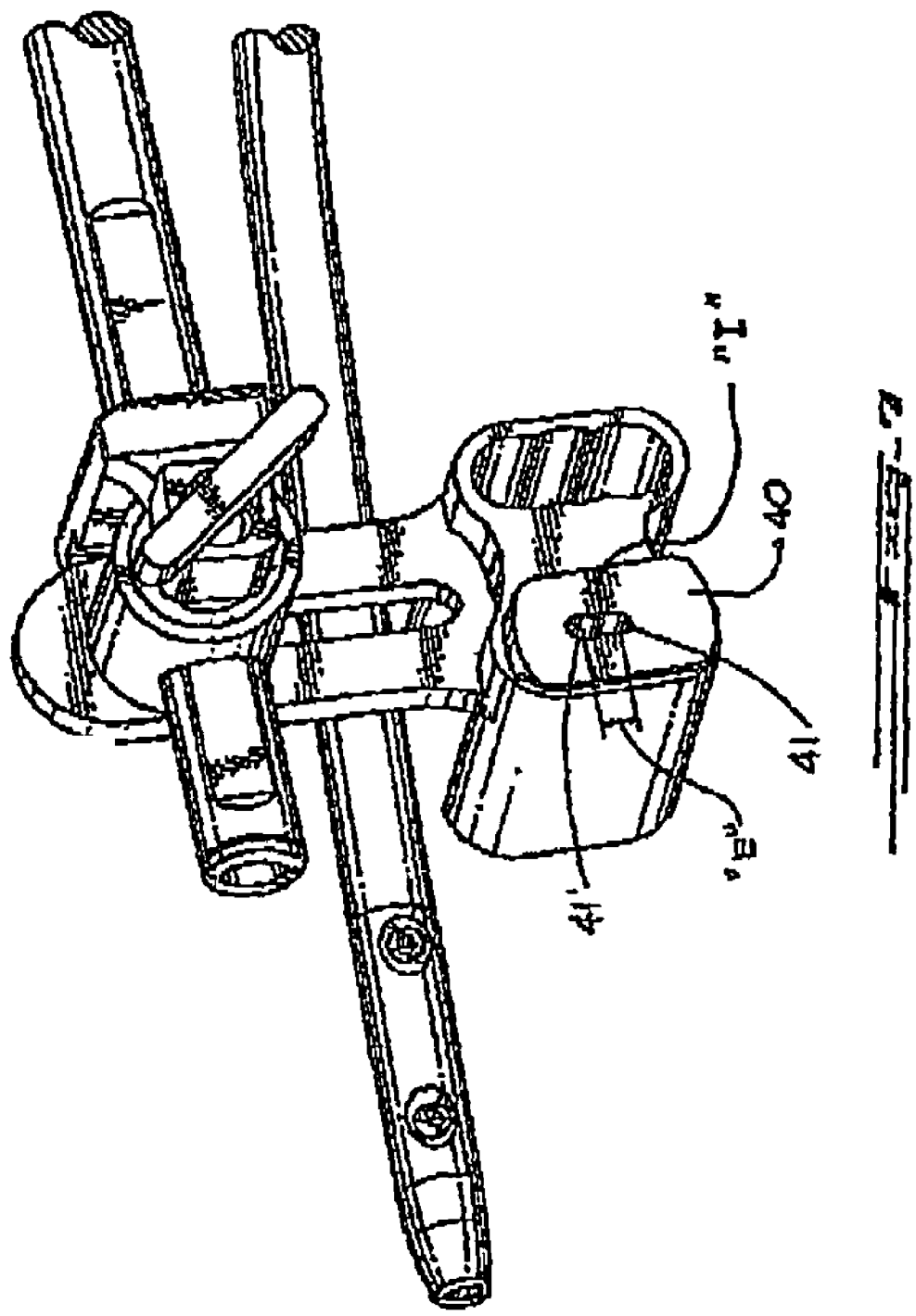

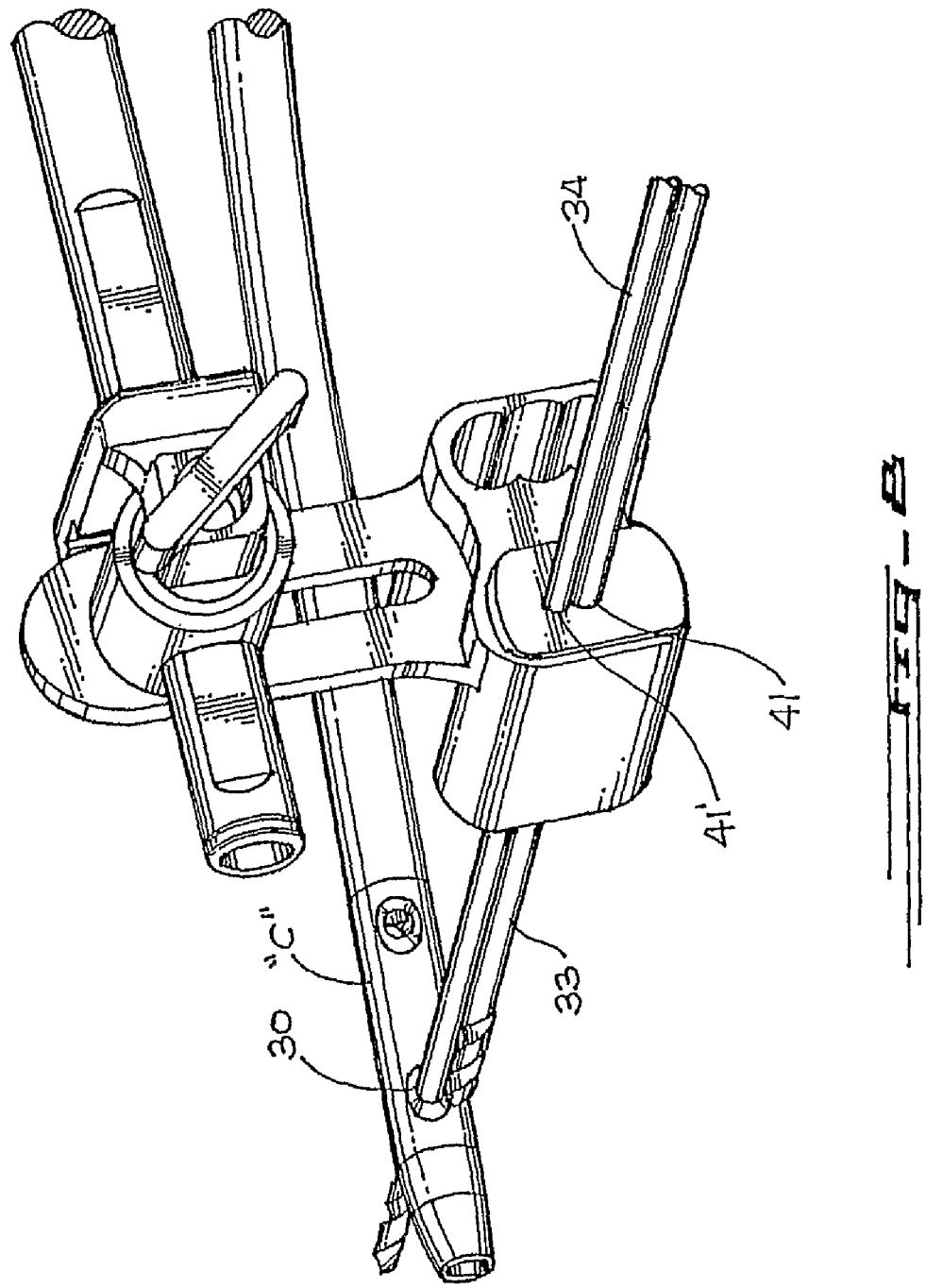

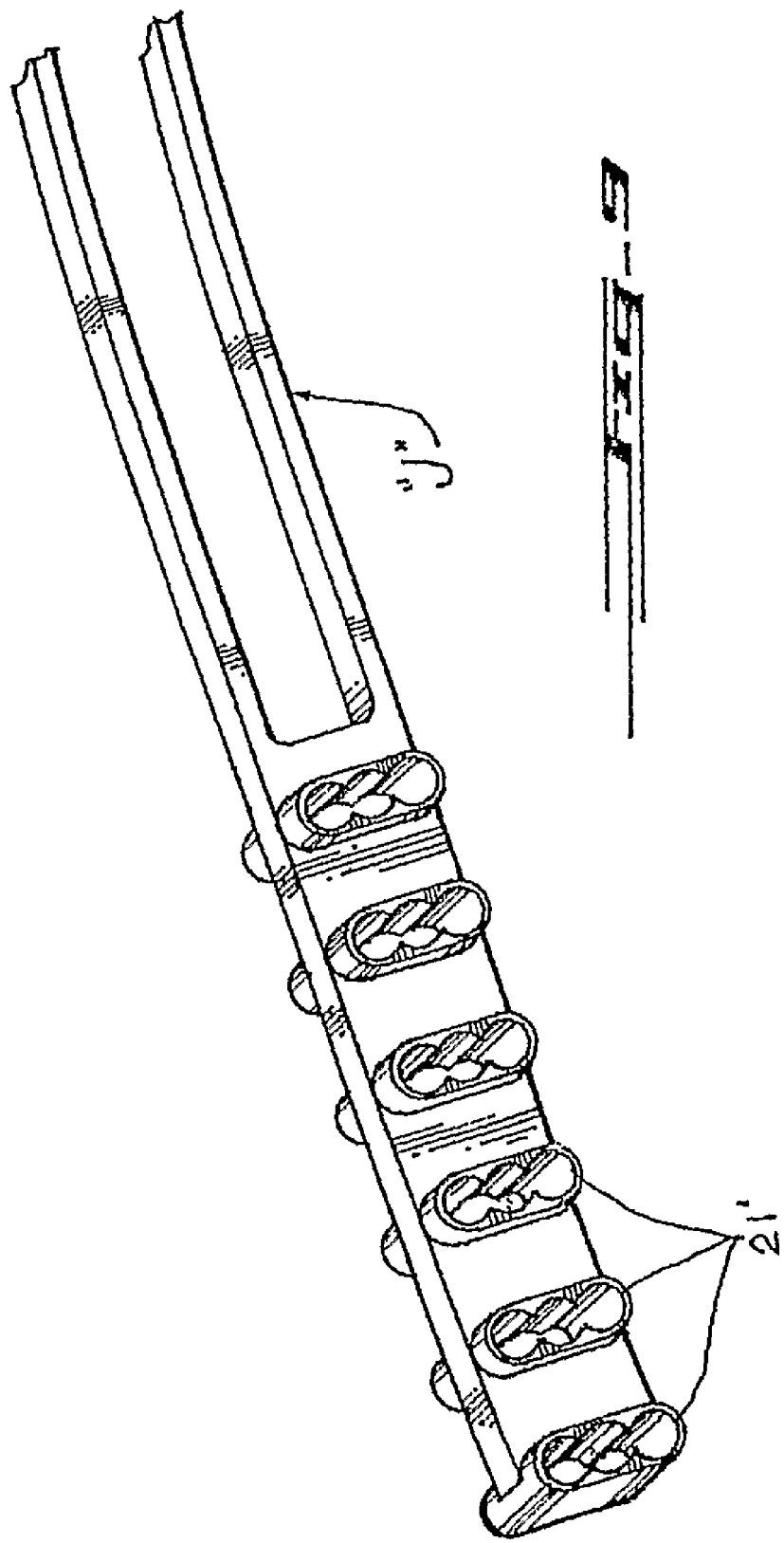

INTRAMEDULLARY NAIL DISTAL TARGETING DEVICE

FIELD OF THE INVENTION

The present invention relates in general to external targeting jig systems, but more particularly to an external jig system that uses a drill guide device connected to the proximal end of an intramedullary nail through a series of attachments. The herein proposed device of the present invention is used for effectively locating the distal screw holes in an intramedullary nail inserted into a fractured bone, without the use of a fluoroscope.

BACKGROUND OF THE INVENTION

It is known to those skilled in the art that an intramedullary nail has a general tendency to bend in the anterior-posterior direction during insertion into the bone, particularly in the femur. The anterior-posterior direction is perpendicular to the screw hole axis, and thus significantly affects the alignment between the drill-guiding hole in the drill guide and the nail screw hole. Medial-lateral bending on the other hand does not significantly affect drill-guiding alignment with the screw hole since the medial-lateral direction is parallel to the axis of the screw hole.

Other distal targeting systems using an external jig utilize some form of drill-guiding hole for each distal screw hole in the nail. The problem with these systems is that since there is no guarantee that the nail will not bend during insertion, there is always a possibility of misalignment between the distal screw hole and the drill-guiding hole, even assuming perfect alignment between the distal screw hole and the drill-guiding hole prior to nail insertion.

It has been observed that in cases where such distal jig systems fail to locate the distal screw hole, the drill (which is passed through the drill-guiding hole) is either anterior or posterior to the distal screw hole, at the same level (or distance from the proximal end of the nail) as the distal screw hole.

It has been further observed that in these cases, the drill is just touching the anterior or posterior surface of the nail when viewed under a fluoroscope. The explanation for this is that when the drill is misaligned with the screw hole, it hits the surface of the nail beside the screw hole. The inherent flexibility of the bone-nail-jig configuration then allows the nail and the drill to slip relative to each other so that the drill slides down to the anterior or posterior surface of the nail.

SUMMARY OF THE INVENTION

The present invention aims to solve the aforementioned problems of the prior art by providing an intramedullary nail distal targeting device that can accurately locate the distal screw holes in an intramedullary nail inserted into a fractured bone without the use of a fluoroscope. Moreover, the herein proposed targeting device of the present invention is provided with novel features that can immediately and accurately correct the alignment of a drill in case the same misses the screw hole of the intramedullary nail during surgery.

The herein proposed invention relates to an intramedullary nail distal targeting device adapted to be installed to an external targeting jig system having a proximal attachment to support said intramedullary nail thereon and an extension arm secured to said proximal attachment, said nail distal targeting device comprising: a drill guide being defined by an abbreviated cylindrical body having at least a pair of guide slots, each of said guide slots having a scalloped inner surface; an attaching means being provided at the upper portion of said drill guide, said attaching means being secured in a rotating and sliding manner to the distal portion of said extension arm; and at least a pair of guide sleeves being telescopically fitted correspondingly into said slots of said drill guide, each of said guide sleeves having a scalloped outer surface to correspondingly fit into said guide slot, each of said guide sleeves being provided with aligned and spaced apart drill-guiding means extending between the opposed end portions thereof.

The present invention further provides a guide sleeve for an intramedullary nail distal targeting device comprising a main tubular body having a sleeve holder being disposed on one end portion thereof, said tubular body having at least a pair of opposed scalloped side portions defining interlocking surfaces therebetween; and a plurality of spaced apart and aligned drill-guiding means extending between the opposed end portions of said tubular body, said drill-guiding means comprising a central drill-guiding hole, and opposed anterior and posterior drill-guiding holes being disposed adjacently with said central drill-guiding hole.

The herein proposed guide sleeve can also be used separately from the external targeting jig system as a separate targeting and aligning instrument.

Other objects and advantages of the preset invention will be set forth in the ensuing detailed description, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

FIG. 6 shows another type of drill used in the present invention;

FIGS. 7, 8 and 9 show another embodiment of the targeting device of the present invention.

DETAILED DESCRIPTION

Referring now to the different views of the drawings, there is shown an intramedullary nail distal targeting device and a guide sleeve therefor designated as 10.

Figure 1A:
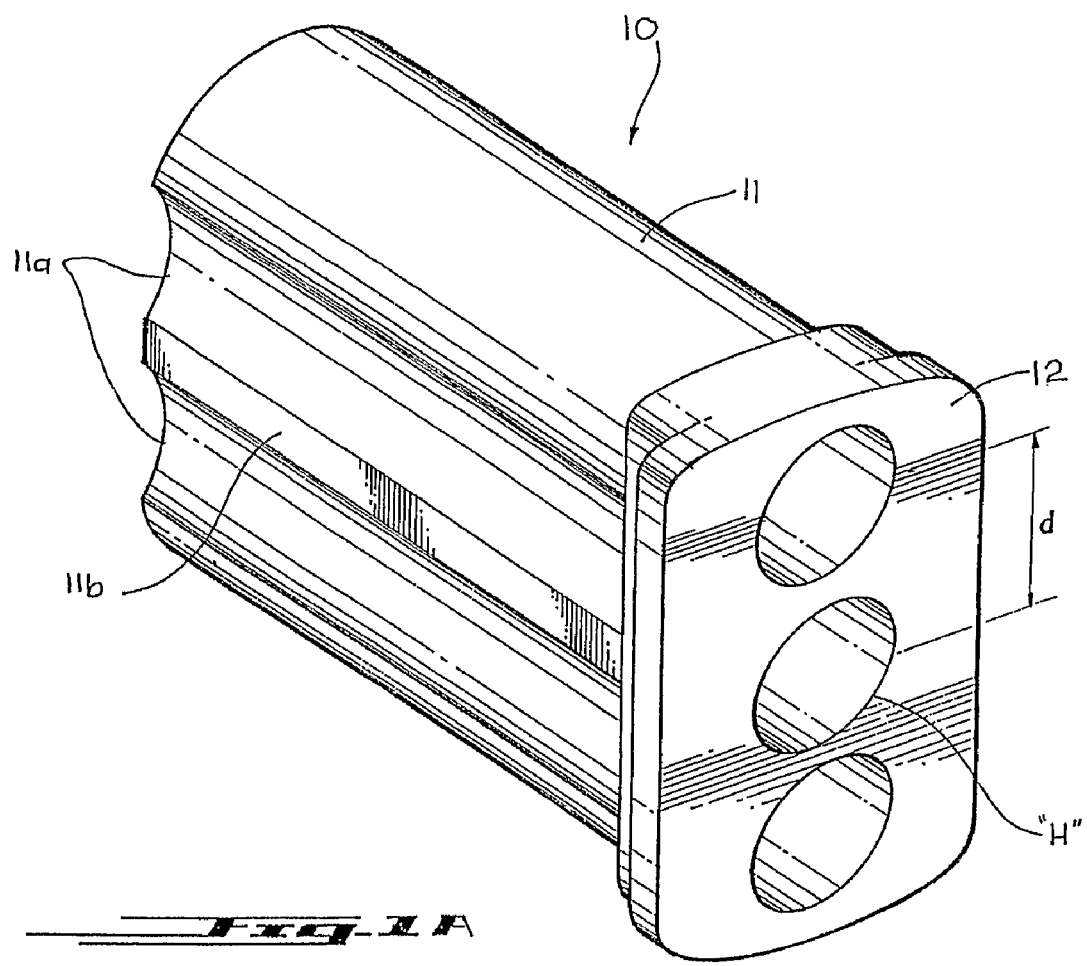
FIG. 1A is a perspective of the guide sleeve of the present invention.
Figure 1B:
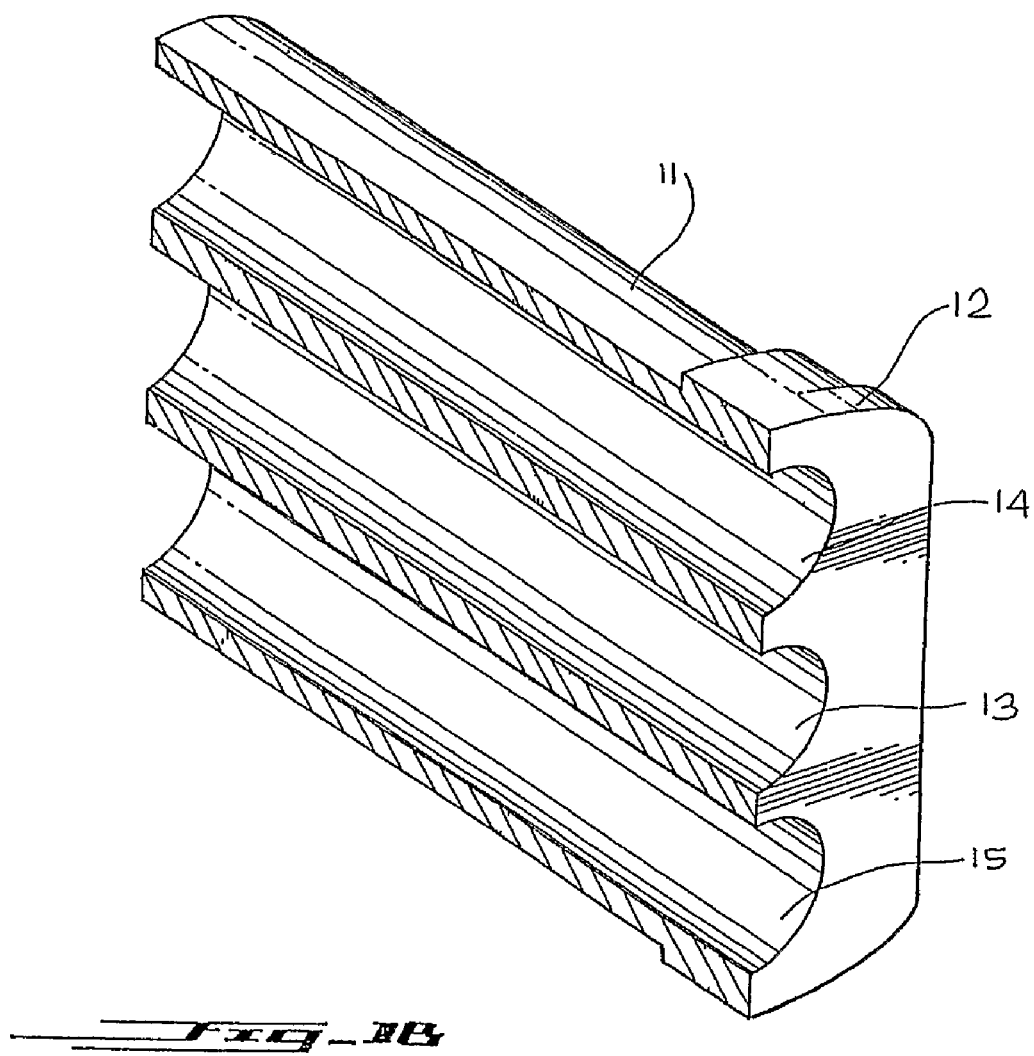
FIG. 1B is a cross sectional view thereof.

As shown FIGS. 1A and 1B, drill sleeve 10 comprises of a main tubular body 11 having a sleeve holder 12 being disposed on one end portion thereof, said tubular body having at least a pair of opposed scalloped side portions 11a defining interlocking surfaces 11b therebetween, and a plurality of spaced apart and aligned drill-guiding means "H" extending between the opposed end portions of the tubular body 11. As further shown in FIG. 1B, drill-guiding hole means "H" comprise of a central drill-guiding hole 13, and a pair of opposed anterior and posterior drill-guiding holes 14 and 15 being disposed adjacently with respect to the central drill-guiding hole 13.

FIGS. 2 to 6 show the preferred embodiment of the present invention for an intramedullary nail distal targeting device 20 adapted to be installed to an external targeting jig system "A" having a proximal attachment "B" to support the intramedullary nail "C" thereon and an extension arm "D" secured to the proximal attachment "B".

The nail distal targeting device 20 comprises of at least one drill guide 21, an attaching means 22 provided at the upper portion of drill guide 21, where the attaching means 22 is secured in a rotating and sliding manner to a distal end of the extension arm "D", and at least a pair of guide sleeves 10 and 10' provided within the drill guide 21.

Drill guide 21 is defined by an abbreviated cylindrical body 23 having at least a pair of guide slots 24 and 24' having scalloped inner surface 25.

The pair of drill sleeves 10 and 10' (which is the guide sleeve embodiment as shown in FIGS. 1A and 1B) is adapted to be telescopically fitted correspondingly into the guide slots 24 and 24' of the drill guide 21. Each of the guide sleeves 10 and 10' is provided with a scalloped outer surface 11a and interconnecting surfaces 11b to correspondingly fit into the guide slots 24 and 24'. Each of the guide sleeves is further provided with aligned and spaced apart drill-guiding means "H" extending between the opposed end portions thereof.

Figure 2:
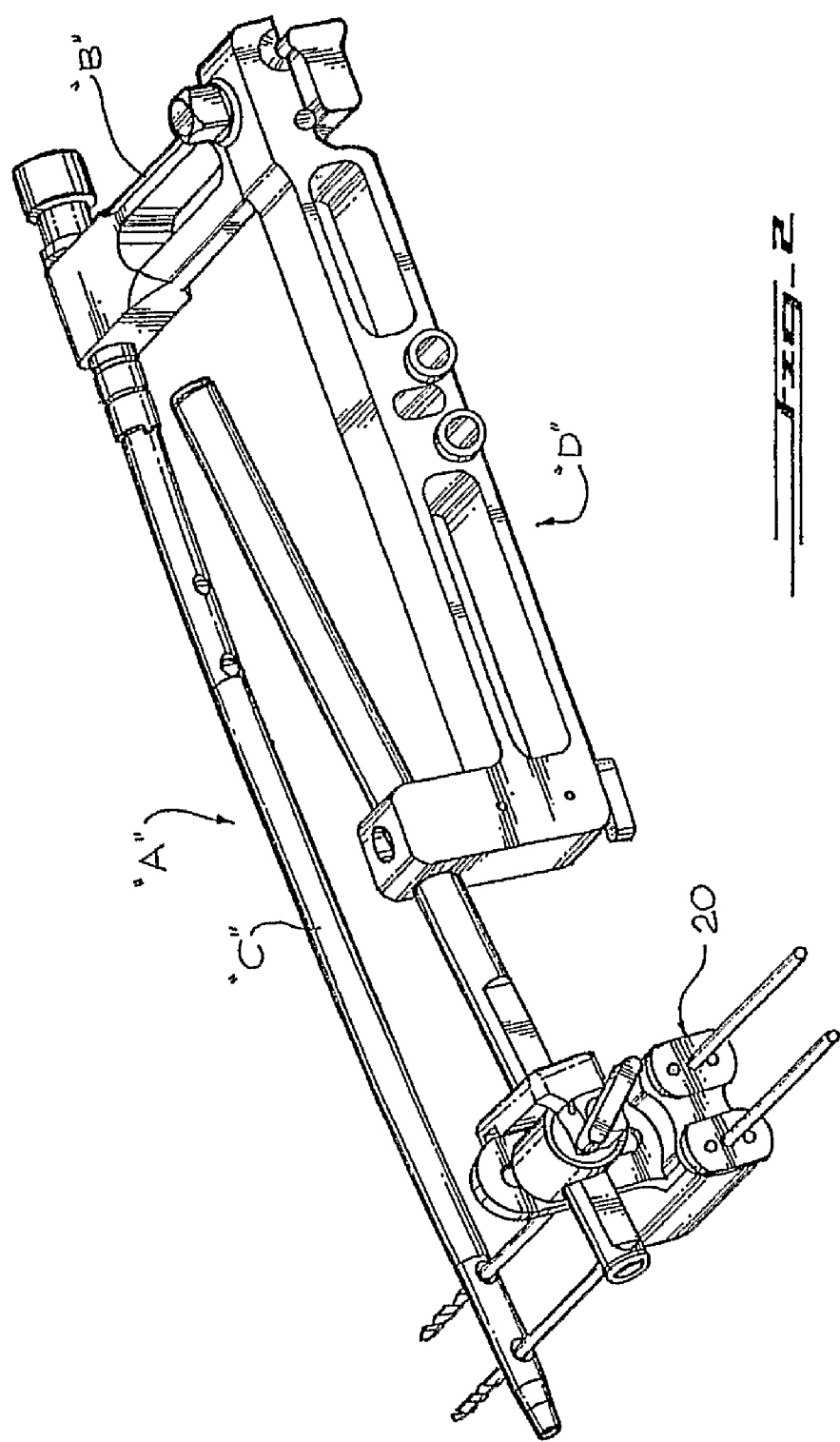
FIG. 2 is a perspective view of the intramedullary nail distal targeting device of the present invention installed to an external targeting jig system.
Figure 3:
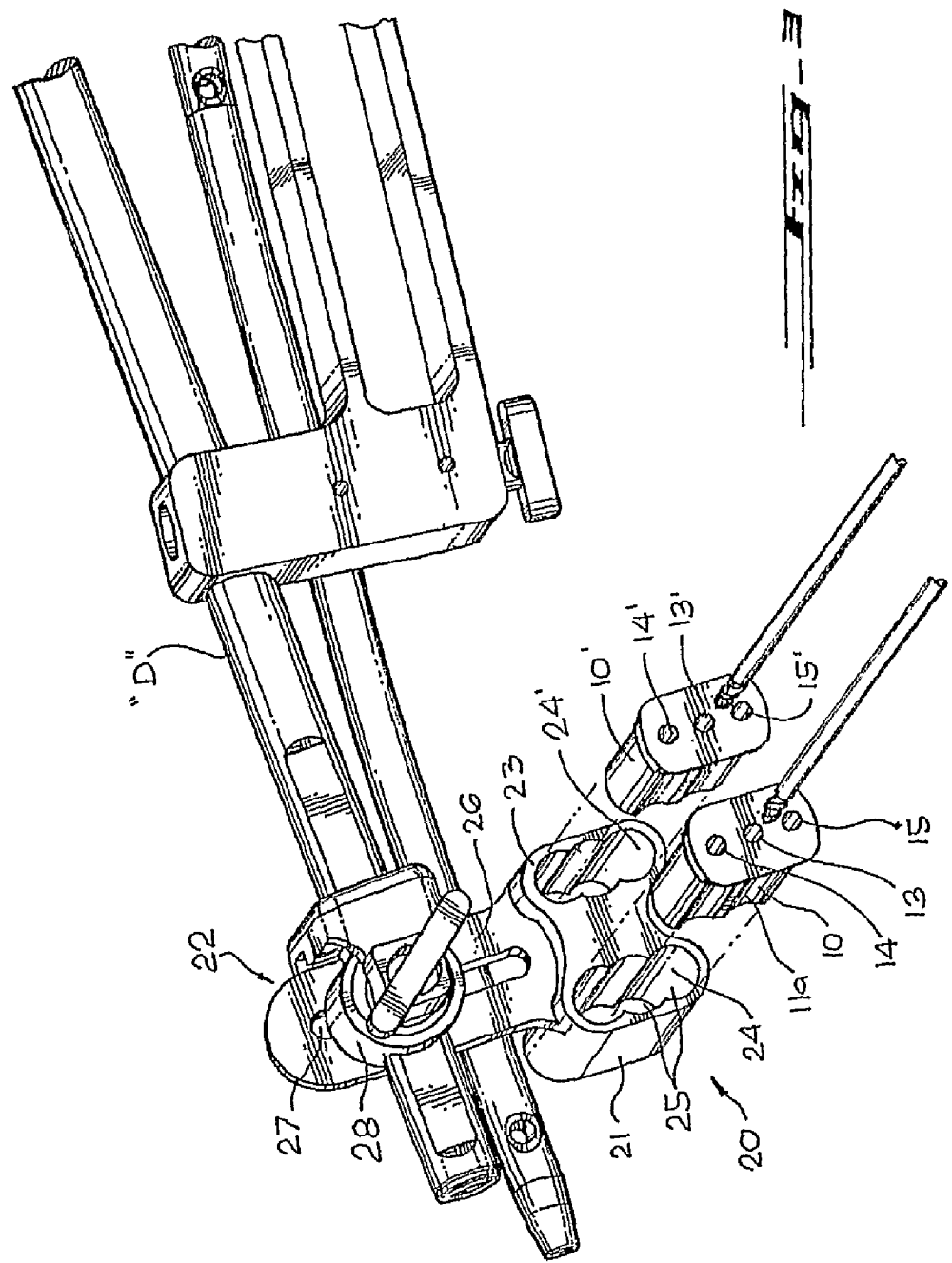
FIG. 3 is an exploded view of the targeting device as attached to a distal end of the extension arm.

In the preferred embodiment of the present invention, the drill-guiding means "H" of the present device as shown in FIG. 3 and in view of FIGS. 1A, 1B and 2, comprises of central drill-guiding holes 13 and 13', and a pair of opposed anterior and posterior drill-guiding holes 14, 14' and 15, 15' disposed adjacently with respect to the central drill-guiding holes 13, 13'. The drill-guiding holes are spaced by a certain distance "d" from each other in the anterior-posterior direction. Distance "d" is approximately one-half (½) the diameter of intramedullary nail "C". The distance "d" has been approximated in order easily locate a screw hole in case the drill misses and is off from the center of the screw hole as will be shown in the ensuing description.

As shown in FIGS. 7 and 8, a drill sleeve 40 is provided with drill-guiding means "I" comprising of a pair of overlapping drill-guiding holes 41 and 41'.

The attaching means 22 as shown in the drawings is adapted to rotate and slide the drill guide 21 to allow the same to be adjusted to the desired or required position. The attaching means 22 comprises of a vertical bracket 26 extending from the upper portion of the drill guide 21 and a clamping member 28 connected to the vertical bracket 26 through central slot 27 provided thereon. The clamping member 28 is further connected to the extension arm "D".

In another embodiment of the present invention as shown FIG. 9, an alternative extension arm "J" is provided with a plurality of spaced apart guide slots 21' being secured thereon. Each of the guide slots 21' function in the same manner as guide slots 24 and 24' as shown in FIG. 3.

Figure 5:
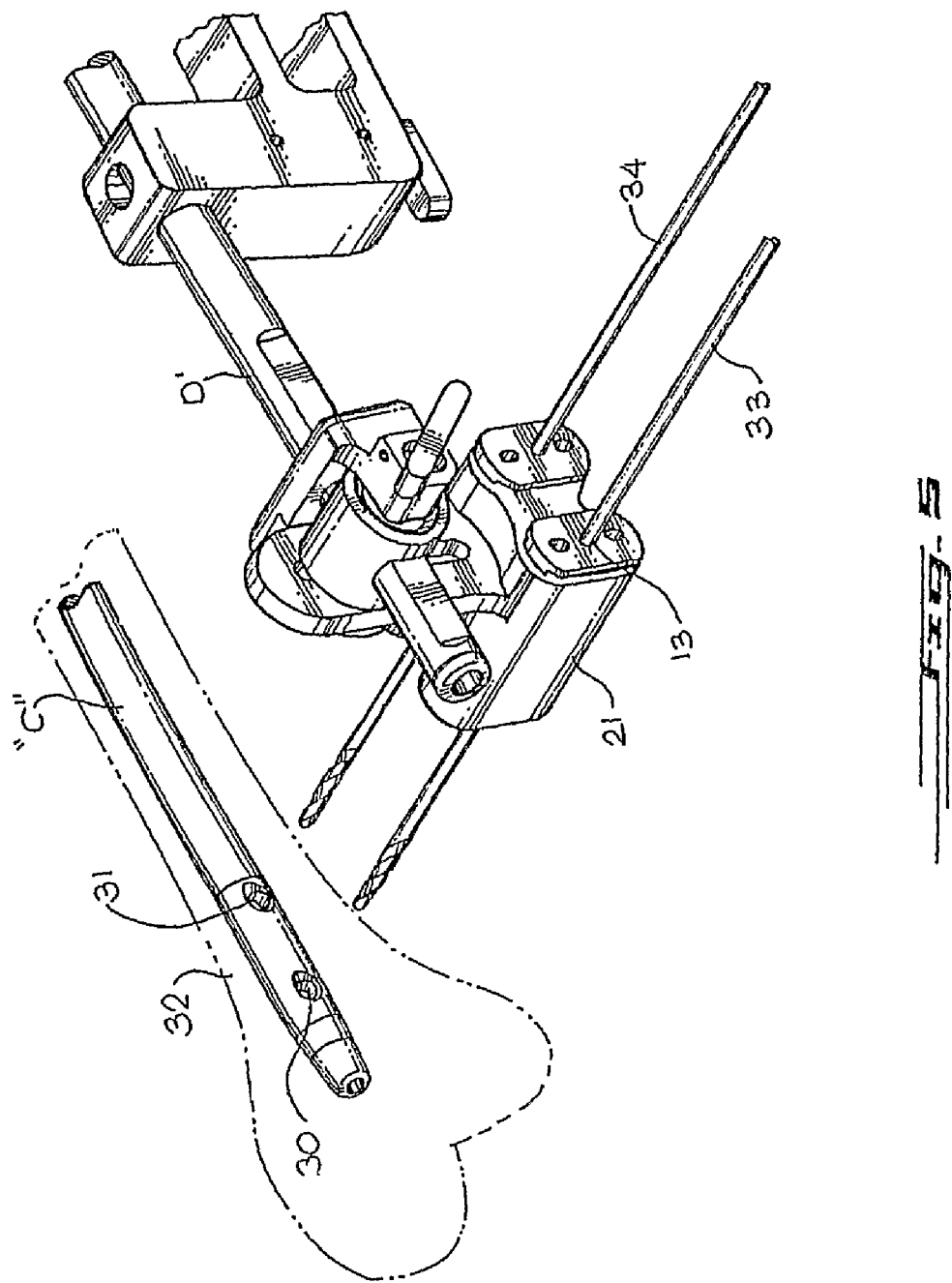
FIG. 5 is a perspective view showing how the drills are targeted on the screw holes of the nail.

To use the device of the present invention, the central drill-guiding holes 13 and 13' are first aligned with distal screw holes 30 and 31 of nail "C", prior to nail insertion into the bone (see FIGS. 3 and 5). Drill guide 21 is then tightened on adjustable arm D' of extension arm "D". After nail "C" is inserted into bone 32, the drill 33 is drilled through central drill-guiding hole 13 of drill sleeve 10 using drill 33. If drill 33 goes through screw hole 30 in nail "C", then screw hole 31 is drilled through central drill-guiding hole 13' using drill 34.

Figure 4:
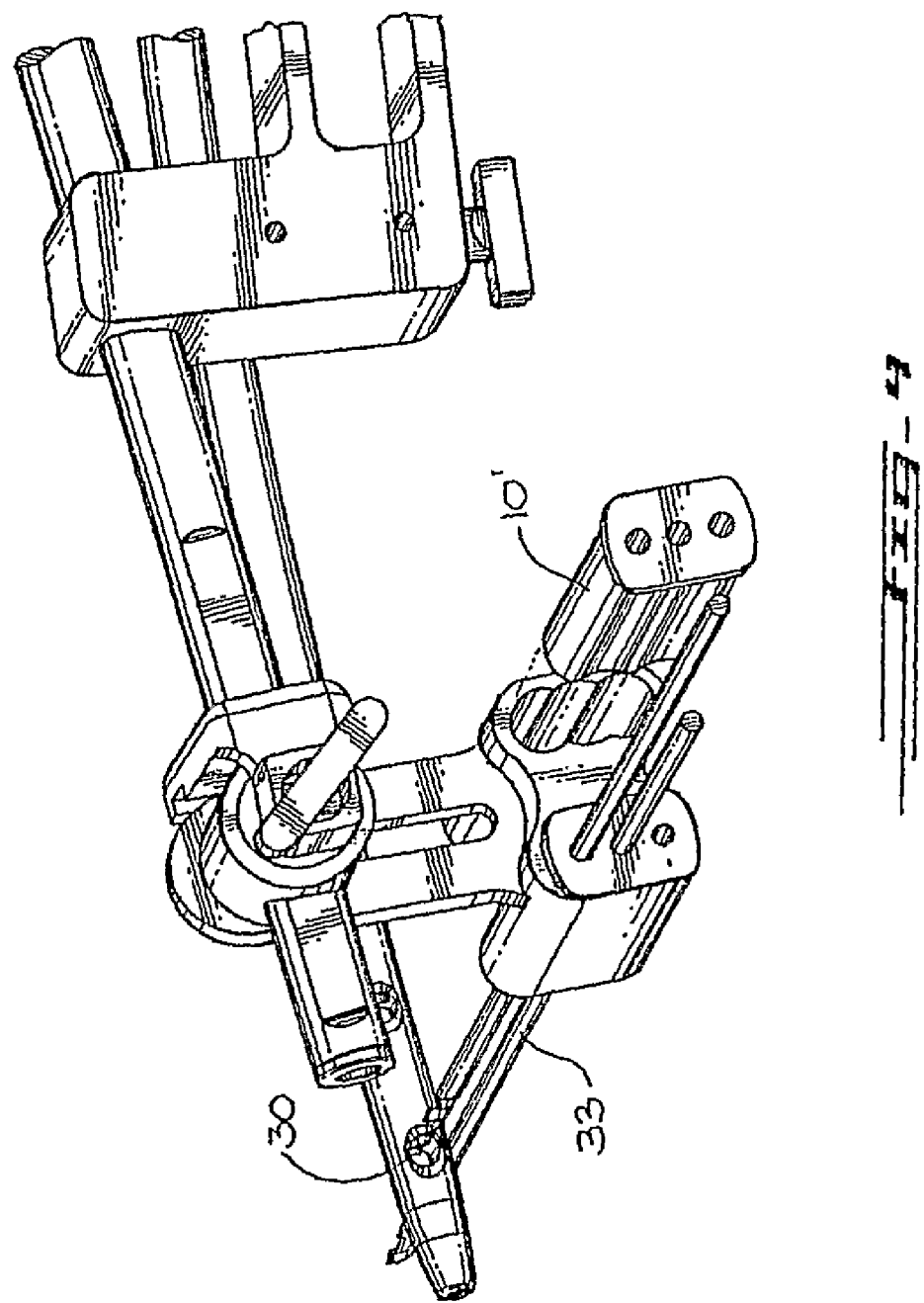
FIG. 4 is an exploded view showing the anterior drill-guiding hole as used to correct the alignment when a drill misses the screw hole of a nail.

After drilling the bone, drill sleeves 10 and 10' are removed and interlocking screws are inserted in the usual manner known to those skilled in the art. A screw sleeve may be inserted through the appropriate spaces in slots 24 and 24' of drill guide 21 to protect the soft tissues while inserting the screw. If the first attempt at targeting screw hole 30 by drilling through drill-guiding hole 13 misses, either one or both drill-guiding holes 14 and 15 are used to drill bone 33 to locate screw hole 30 in nail "C". This is done while drill 33 is still embedded in bone 32 (FIG. 4). After screw hole 30 is located, screw hole 31 is then located using the corresponding anterior or posterior drill-guiding hole (i.e., drill-guiding hole 14 corresponds to drill-guiding hole 14', and drill-guiding hole 15 corresponds to drill-guiding hole 15'). Since the distance between the drill-guiding holes is a distance "d" which is approximately one half (½) the diameter of the nail, location of the missed screw hole can easily be attained as described in the previous method. The size of the drill-guiding holes in drill sleeves 10 and 10' is shown in the figures to accommodate the drill directly. This is done only for simplicity of presentation. Preferably, the drill-guiding holes should be designed to accommodate a tube-like drill sleeve with an internal diameter that will fit the drill. The drill sleeve serves as a soft tissue protector while drilling.

In order to minimize the potential damage to the bone caused by drilling multiple holes (in the event that drilling through the first central drill-guiding hole misses the screw hole in the nail), a small diameter drill, or similar tool may be used to first locate the distal screw holes in the nail. After the screw holes are located, the holes in the bone are enlarged using a larger drill to accommodate the interlocking screw. In the illustration shown in FIG. 6, a pin 35 with a turned-down portion 35a is used instead of a small diameter drill. The turned-down portion 35a has a small diameter and has a cutting end 35b.

A further way to minimize the damage to the bone is to minimize the number of holes used in locating the distal screw holes. If the first drilling attempt misses the distal screw hole, the incision on the skin may be enlarged to expose approximately the full diameter of the bone. The direction for the second drill hole (anterior or posterior) relative to the first drill hole should be towards the center of the bone diameter. Alternatively, an X-ray can be taken, and the direction for the second hole is determined from the X-ray film.

The preceding discussions assume that in the first attempt to locate the screw hole, the drill will either go through the screw hole, or miss the screw hole and slip to the anterior or posterior surface of the nail. However, it is also possible that the drill will not slip relative to the nail. This can happen if the nail is tight inside the bone, and it does not have enough space inside the bone to move in the direction that will cause slipping between the drill and the nail. In this case, a different type of drill sleeve is used.

Referring now to FIGS. 7 and 8, drill sleeve 40 is formed by an abbreviated cylindrical body with corresponding scalloped external surface and provided with the overlapping drill-guiding holes 41 and 41'. The overlapping drill-guiding hole 41 is centered on drill sleeve 40, while drill-guiding hole 41' is offset to one side by a distance "E" approximately equal to one fourth the diameter of nail "C". If when drilling though drill guiding-hole 13 of drill sleeve 10, drill 33 neither goes through screw hole 31 nor slips to the anterior or posterior surface of nail "C", drill sleeve 10 is removed and drill sleeve 40 is placed inside slot 24 of drill guide 21 such that drill 33 (still embedded in the bone) goes through drill-guiding hole 41. The second drill 34 is then used to drill through drill guiding hole 41'. Drill 34 will either go through screw hole 30 or slip to the anterior or posterior surface of nail "C". After drill 34 is drilled into the bone, drill 33 is removed from the bone, and drill sleeve 40 is removed from slot 24. Drill sleeve 10 with the three drill-guiding holes is then inserted into slot 24 such that drill 34 goes through central drill-guiding hole 13 of drill sleeve 10. Due to its inherent flexibility, the assembly composed of proximal attachment "B" and extension arm "D" will bend to allow central drill-guiding hole 13 to align with drill 33. This configuration of the bone-nail-jig assembly is now the same as the configuration where the first drill used to drill the first hole in the bone either goes through the screw hole or slips to the anterior or posterior surface of the nail. The succeeding steps will therefore be the same as discussed in the previous paragraphs.

Drill guide 21 as shown in FIGS. 1 to 8 is designed to be adjustable relative to extension arm "D" so that it can be aligned accurately with distal screw holes 30 and 31 of nail "C".

Alternatively, the drill guide can be fixed relative to an alternative extension arm "J" as shown in FIG. 9. In this embodiment, an alternative extension arm "J" is provided with a plurality of spaced apart guide slots 21' being secured thereon corresponding to different nail lengths. Each of the guide slots 21' is defined by an abbreviated generally cylindrical body having a scalloped inner surface. The alternative extension arm "J" will not have any provision for rotation or sliding. The guide slots 21' will be fixed relative to the extension arm. The position of the guide slots 21' will already take into account the curvature of the nail as well as the different nail lengths.

Another alternative embodiment is to have the drill guide and extension arm fixed to the proximal attachment. In this embodiment, the proximal attachment, extension arm, and drill guide become one solid piece.

The present invention can be applied to an antegradely inserted femoral or tibial nail, as well as to a retrogradely inserted femoral nail. For a retrogradely inserted femoral nail, the screw holes to be targeted will be the proximal screw holes instead of the distal screw holes. Although the discussions above focus on the application for locating holes whose axes are in the medial-lateral direction, the same inventive concept can also be applied for locating holes oriented in other directions, for example, in the anterior-posterior direction. Finally, the present invention can also be applied for locating the screw holes in humeral nails.

It is also possible to conceive of the same drill guide with multiple drill-guiding holes as discussed above to be used with other distal hole targeting systems whether or not such targeting systems are used with a fluoroscope. For example, some targeting systems make use of a jig that is mounted on the fluoroscope. Other jigs are mounted on the proximal end of the nail, but they are used with a fluoroscope. The drill guide 21 of the present invention can be used with these types of jigs.

It is also possible to use the drill sleeve 10 in the free-hand technique of distal targeting using a fluoroscope, as known to those skilled in the art. In this case, the drill sleeve can be used to aid in locating the screw hole if the first attempt at targeting with the free-hand technique misses the screw hole. The central drill-guiding hole of the drill sleeve can be placed over the drill used in the first attempt, and then the screw hole is drilled through either the anterior or posterior drill-guiding hole of the drill guide.

Alternatively, when used in the free-hand technique, the drill guide 21 can have just two adjacent drill-guiding holes instead of three. One of the two drill-guiding holes is place over the first drill such that the other drill-guiding hole is towards the correct direction (anterior or posterior) as seen on the fluoroscope.

Additional advantages and modifications of the present invention will readily occur to those skilled in the art in view of these teachings. The present invention in its broader aspects is not limited to the specific details, representative contrivances, and illustrative examples shown and described herein. Accordingly, various modifications may be made without departing from the spirit and scope of the general inventive concept as defined in the appended claims and their equivalents.

The invention claimed is:

1. An intramedullary nail distal targeting device adapted to be installed to an external targeting jig system having a proximal attachment to support an intramedullary nail thereon and an extension arm having a longitudinal axis, wherein the extension arm is secured to said proximal attachment, said nail distal targeting device comprising:
   at least one drill guide being secured to said extension arm, said drill guide being defined by an abbreviated cylindrical body having at least a pair of guide slots, each of said guide slots having a scalloped inner surface;
   an attaching means being provided at the upper portion of said drill guide and comprising a rotation axis, said attaching means being secured in a rotating and sliding manner to a distal end of said extension arm so that the rotation axis intersects the longitudinal axis of the extension arm; and
   at least a pair of drill sleeves being telescopically fitted correspondingly into said guide slots of said drill guide, each of said drill sleeves having a scalloped outer surface to correspondingly fit into said guide slot, each of said drill sleeves being provided with aligned and spaced apart drill-guiding means extending between the opposed end portions thereof.

2. An intramedullary nail distal targeting device in accordance with claim 1, wherein said drill-guiding means comprises a central drill-guiding hole, and a pair of opposed anterior and posterior drill-guiding holes being disposed adjacently with said central drill-guiding hole.

3. An intramedullary nail distal targeting device in accordance with claim 2, wherein the distance between said central drill-guiding hole and said opposed anterior and posterior drill-guiding holes is approximately one-half (½) the diameter of said intramedullary nail.

4. An intramedullary nail distal targeting device in accordance with claim 1, wherein said drill-guiding means comprises a pair of overlapping drill-guiding holes.

5. An intramedullary nail distal targeting device in accordance with claim 1, wherein said attaching means comprises a vertical bracket extending from said drill guide and a clamping member means connected to said vertical bracket and said extension arm.

* * * * *